US012779129B2

(12) United States Patent
Smith

(10) Patent No.: US 12,779,129 B2
(45) Date of Patent: Nov. 3, 2026

(54) WIRELESS DATA COMMUNICATION CIRCUITRY FOR A DRUG DELIVERY DEVICE

(71) Applicant: Sanofi, Paris (FR)

(72) Inventor: Ronald Antony Smith, Warwick (GB)

(73) Assignee: SANOFI, Paris (FR)

( * ) Notice: Subject to any disclaimer, the term of this patent is extended or adjusted under 35 U.S.C. 154(b) by 1079 days.

(21) Appl. No.: 17/783,079

(22) PCT Filed: Dec. 11, 2020

(86) PCT No.: PCT/EP2020/085734
§ 371 (c)(1),
(2) Date: Jun. 7, 2022

(87) PCT Pub. No.: WO2021/116393
PCT Pub. Date: Jun. 17, 2021

(65) Prior Publication Data

US 2023/0001097 A1 Jan. 5, 2023

(30) Foreign Application Priority Data

Dec. 13, 2019 (EP) .................................... 19306644

(51) Int. Cl.
*A61M 5/315* (2006.01)
*H04W 4/80* (2018.01)

(52) U.S. Cl.
CPC .......... *A61M 5/31553* (2013.01); *H04W 4/80* (2018.02); *A61M 2205/3584* (2013.01); *A61M 2205/8212* (2013.01)

(58) Field of Classification Search
CPC ...... A61M 5/31553; A61M 2205/3584; A61M 2205/8212
See application file for complete search history.

(56) References Cited

U.S. PATENT DOCUMENTS

2002/0040208 A1* 4/2002 Flaherty ............ A61M 5/14248 604/67
2007/0040449 A1 2/2007 Spurlin et al.
(Continued)

FOREIGN PATENT DOCUMENTS

EP 3522329 A1 8/2019
JP 2010106847 A 5/2010
(Continued)

OTHER PUBLICATIONS

Notice of Reasons for Refusal, JP Patent Application No. 2022535480, dated Aug. 6, 2024, pp. 1-11 (with pp. 1-6 being a translation).
(Continued)

*Primary Examiner* — Dung T Ulsh
(74) *Attorney, Agent, or Firm* — Bond, Schoeneck & King, PLLC

(57) ABSTRACT

A wireless data communication circuitry for a drug delivery device is disclosed, wherein the circuitry comprises a wireless communication processor for handling wireless data communication, a battery connector having a positive and a negative terminal, the positive terminal and the negative terminal being connected to respective terminals of the wireless communication processor for supplying the wireless communication processor with electrical energy from a battery connectable to the battery connector, and an arrangement of one or more capacitors, each one of the capacitors being connected in parallel to the positive terminal and the negative terminal of the battery connector and provided for backing up the supplying of the wireless communication processor with electrical energy from the battery connectable to the battery connector.

13 Claims, 3 Drawing Sheets

(56) References Cited

U.S. PATENT DOCUMENTS

| | | | | |
|---|---|---|---|---|
| 2010/0159293 | A1 | 6/2010 | Hempel | |
| 2014/0276583 | A1* | 9/2014 | Chen ................. | A61M 5/31546 604/207 |
| 2019/0134305 | A1 | 5/2019 | Srinivasan et al. | |
| 2022/0040401 | A1* | 2/2022 | Quintanar ............. | A61M 1/913 |

FOREIGN PATENT DOCUMENTS

| | | | |
|---|---|---|---|
| JP | 2016040980 | A | 3/2016 |
| JP | 2017502585 | A | 1/2017 |
| JP | 2019106847 | A | 6/2019 |
| KR | 100563701 | B1 | 3/2006 |
| WO | WO 2019/036576 | | 2/2019 |
| WO | 2019121608 | A1 | 6/2019 |
| WO | WO 2019/121613 | | 6/2019 |
| WO | 2019164936 | A1 | 8/2019 |
| WO | WO 2019/219824 | | 11/2019 |

OTHER PUBLICATIONS

Second Office Action, CN Patent Application No. 202080086057.1, dated Aug. 20, 2024, pp. 1-15 (with pp. 1-9 being a translation).

International Preliminary Report on Patentability in International Appln. No. PCT/EP2020/085734, mailed on Jun. 23, 2022, 8 pages.

International Search Report and Written Opinion in International Appln. No. PCT/EP2020/085734, mailed on Jan. 22, 2021, 10 pages.

* cited by examiner

WIRELESS DATA COMMUNICATION CIRCUITRY FOR A DRUG DELIVERY DEVICE

CROSS REFERENCE TO RELATED APPLICATIONS

The present application is the national stage entry of International Patent Application No. PCT/EP2020/085734, filed on Dec. 11, 2020, and claims priority to Application No. EP 19306644.6, filed on Dec. 13, 2019, the disclosures of which are incorporated herein by reference.

TECHNICAL FIELD

The present disclosure relates to a wireless data communication circuitry for a drug delivery device, particularly a drug injection device.

BACKGROUND

A variety of diseases exists that require regular treatment by delivery, particularly injection of a medicament. Such injection can be performed by using injection devices, which are applied either by medical personnel or by patients themselves.

Drug delivery devices particularly for usage by patients themselves may be equipped with electronics for measuring and storing data related to the usage. The usage related data may also be transmitted via a wireless link or a wireline connection to an external device such as a smartphone, a tablet or laptop computer, or in the cloud. For example, US 2019/0134305 A1 discloses a medication delivery device, for example an injection pen or a wearable pump, which can be paired with an external device for providing data captured from a flow sensor relating to medicine delivery to a patient to a paired external device. The device can have Bluetooth® communication and/or near field communication (NFC) circuits for proximity-based pairing and connectivity with the external device for real-time or deferred transfer of captured data to the external device.

Another drug delivery device is disclosed e.g. in WO2019036576A1. It contains a microcontroller unit to wirelessly transmit a signal representative of a detected dose to a paired remote electronic device e.g. via Bluetooth.

An accessory for attachment to a drug delivery device is disclosed e.g. in WO2019/219824. Transmission of data via NFC or Bluetooth from the accessory to an external device is described.

SUMMARY

In one aspect the present disclosure provides a wireless data communication circuitry for a drug delivery device comprising a wireless communication processor for handling wireless data communication, a battery connector having a positive and a negative terminal, the positive terminal and the negative terminal being connected to respective terminals of the wireless communication processor for supplying the wireless communication processor with electrical energy from a battery connectable to the battery connector, and an arrangement of one or more capacitors, each one of the capacitors being connected in parallel to the positive terminal and the negative terminal of the battery connector and provided for backing up the supplying of the wireless communication processor with electrical energy from the battery connectable to the battery connector. The wireless communication processor may be configured to handle wireless data communication according to one or more wireless communication technologies, particularly low power wireless communication technologies including RF-based technologies such as Bluetooth® Low Energy, ANT (Adaptive Network Technology) from ANT Wireless, ZigBee™, NFC (Near Field Communication), Wi-Fi™. It turns out that the battery life for operating a wireless communication processor can be extended with connecting an arrangement of one or more capacitors in parallel to the positive and terminal of the battery connector. Particularly, this arrangement of capacitors may extend battery life with low power wireless communication technologies, which employ a kind burst mode data transmission periodically after several seconds or within a second.

In embodiments, each one of the capacitors is permanently connected in parallel to the positive and the negative terminal of the battery connector. Thus, the one or more capacitors are not "switched" out of the circuitry but are permanently connected. This allows the one or more capacitors to settle to a much a lower leakage current than it may be considered to be possible.

In embodiments, the wireless communication processor may particularly comprise a Bluetooth® communication circuitry with an antenna configured for Bluetooth® communication, wherein the Bluetooth® communication circuitry comprises a Bluetooth® Low Energy radio circuitry for wireless data communication.

In more specific embodiments, the arrangement of one or more capacitors may consist of four capacitors or five capacitors. Experiments have shown that an arrangement of four or five capacitors, particularly with different capacities, may increase battery life such that requirements of drug delivery devices and their duration of usage may be well met.

In a specific embodiment, the arrangement of four capacitors or five capacitors may comprise two capacitors with a capacity of 220 microfarads and two or three capacitors with a capacity of 47 microfarads. Such an arrangement has been proven to be a suitable solution for extending the battery life of a typical button cell such as the cell type CR1225 with a terminal voltage around 3 volts and a capacity of about 48 milliampere-hour.

In specific embodiments, the arrangement of one or more capacitors may also comprise one or more of the following: a ceramic capacitor; a film capacitor; a polymer capacitor; a mica capacitor; an electrolytic capacitor; a tantalum capacitor. Particularly, a ceramic capacitor has a relatively low ESR (equivalent series resistance) and typically no ripple current limitations, and, thus, may be well suited for backing up the power supply of the wireless communication processor by a battery such as button cell.

In specific embodiments, the circuitry may be arranged on a printed circuit board (PCB) configured to be arranged in a drug delivery device, particularly a drug injection pen, or in an accessory to be attached to a drug injection pen. Particularly, the PCB may be implemented by two smaller PCBs, on which the entire electronics of the drug delivery device may be arranged and connected including the wireless communication processor, the battery connector and the arrangement of one or more capacitors.

In a further aspect, the present disclosure provides electronics for a drug delivery device, wherein the electronics comprises a PCB with a wireless data communication circuitry as disclosed herein and being arranged on the PCB. The electronics may be particularly designed to be located in a body of a drug delivery device, in a dosage knob of the drug delivery device or in a body of an accessory for attachment to a drug delivery device. For example, the shape of the PCB of the electronics may be designed so that the electronics can be integrated in a component of a drug delivery device or in an accessory's body.

In some embodiments, the electronics may comprise a battery connected to the battery connector, wherein the battery is a button cell, particularly a lithium button cell battery, having a capacity of several milliampere-hour, e.g. about 48 milliampere-hour, with a terminal voltage around 3 volts.

In a yet further aspect, the present disclosure provides a drug delivery device comprising a wireless data communication circuitry comprising:

- a wireless communication processor for handling wireless data communication,
- a battery connector having a positive and a negative terminal, the positive terminal and the negative terminal being connected to respective terminals of the wireless communication processor for supplying the wireless communication processor with electrical energy from a battery connectable to the battery connector, and
- an arrangement of one or more capacitors, each one of the capacitors being connected in parallel to the positive terminal and the negative terminal of the battery connector and provided for backing up the supplying of the wireless communication processor with electrical energy from the battery connectable to the battery connector.

The drug delivery device may further comprise a body, a dosage selection mechanism for selecting a drug dosage to be delivered, a dispensing mechanism for delivering a selected drug dosage, at least one antenna for wireless communication, and electronics as disclosed herein, wherein the wireless data communication circuitry of the electronics is coupled to the at least one antenna. The drug delivery device may further comprise a holder for holding a drug container, e.g. a cartridge holder.

The antenna and/or the electronics may be arranged within an actuator, e.g. a dosage knob of the drug delivery device. The dosage knob may be configured for setting a dose to be dispensed by a user rotating the dosage knob. The dosage knob may be configured for dispensing a set dose by a user pressing on the dosage knob. The dosage knob may comprise a separate push button/injection button or may be dial grip and injection button in one piece.

The drug delivery device may be a reusable device, with a typical life cycle of several years. The employed electronics may allow using the drug delivery device for the typical life cycle without changing the battery. The drug delivery device is equipped by the electronics with the ability to wirelessly exchange data with another device such as mobile phone, particularly a smartphone, a computer, particularly a Personal Computer (PC), a tablet computer, a laptop computer.

According to a further aspect, the drug delivery device may comprise a dose setting member rotatable relative to the body during dose delivery. A sensed element may be rotationally fixed to the dose setting member. The drug delivery device may further comprise an actuator which is axially movable, but not rotatable relative to the body of the drug delivery device during dose delivery. The actuator may be axially and rotationally fixed to the dose setting member during dose setting. The actuator may comprise at least one rotation sensor responsive to relative rotation of the sensed element and the actuator during dose delivery. The actuator may further comprise electronics with a wireless data communication circuitry comprising:

- a wireless communication processor for handling wireless data communication,
- a battery connector having a positive and a negative terminal, the positive terminal and the negative terminal being connected to respective terminals of the wireless communication processor for supplying the wireless communication processor with electrical energy from a battery connectable to the battery connector, and
- an arrangement of one or more capacitors, each one of the capacitors being connected in parallel to the positive terminal and the negative terminal of the battery connector and provided for backing up the supplying of the wireless communication processor with electrical energy from the battery connectable to the battery connector.

The actuator may comprise at least one rotation sensor responsive to relative rotation of a sensed element and the actuator during dose delivery. The electronics may comprise a controller responsive to said rotation sensor to detect the amount of rotation of the sensed element relative to the actuator during dose delivery.

The electronics may be responsive to the rotation sensor to determine the amount of drug delivered based on the detected amount of rotation of the sensed element relative to the actuator during dose delivery.

The at least one rotation sensor may be an optical, magnetic or an acoustic sensor.

The sensed element may include alternating first and second surface features circumferentially spaced around a dose setting member of a drug delivery device.

The rotation sensor may include a light source emitting light during dose delivery and a light sensor to detect light reflected on the surface features of the sensed element or transmitted by certain regions of the sensed element.

The wireless communication circuitry may be configured to wirelessly transmit data related to a dose delivered by the drug delivery device to another device such as mobile phone, particularly a smartphone, a computer, In a yet further aspect, the present disclosure provides an accessory for attachment to a drug delivery device comprising electronics with a wireless data communication circuitry comprising

- a wireless communication processor for handling wireless data communication,
- a battery connector having a positive and a negative terminal, the positive terminal and the negative terminal being connected to respective terminals of the wireless communication processor for supplying the wireless communication processor with electrical energy from a battery connectable to the battery connector, and
- an arrangement of one or more capacitors, each one of the capacitors being connected in parallel to the positive terminal and the negative terminal of the battery connector and provided for backing up the supplying of the wireless communication processor with electrical energy from the battery connectable to the battery connector.

The accessory may comprise a housing configured for the attachment to a drug delivery device, at least one antenna for wireless communication being arranged within the housing, and electronics as disclosed herein, wherein the electronics are arranged within the housing and the wireless data communication circuitry of the electronics are coupled to the at least one antenna. The accessory may be designed as a universally applicable device, which can be attached to different drug delivery devices and provide the drug delivery device with the ability to wirelessly exchange data with a another device such as mobile phone, particularly a smartphone, a computer, particularly a Personal Computer (PC), a tablet computer, a laptop computer.

The accessory may comprise at least one rotation sensor configured to detect relative rotation of a sensed element of a drug delivery device and the accessory during dose delivery.

The electronics of the accessory may comprise a controller responsive to the rotation sensor to capture the amount of rotation of the sensed element relative to the accessory during dose delivery.

The electronics may be responsive to the rotation sensor to determine the amount of drug delivered based on a detected amount of rotation of a sensed element of a drug delivery device relative to the accessory during dose delivery.

The at least one rotation sensor may be an optical, magnetic or an acoustic sensor.

The sensed element may include alternating first and second surface features circumferentially spaced around a dose setting member of a drug delivery device.

The rotation sensor may include a light source emitting light during dose delivery and a light sensor to detect light reflected on the surface features of the sensed element or transmitted by certain regions of the sensed element.

The wireless communication circuitry of the accessory may be configured to wirelessly transmit data related to a dose delivered by the drug delivery device to another device such as mobile phone, particularly a smartphone, a computer,

DETAILED DESCRIPTION

In the following, embodiments of the present disclosure will be described with reference to injection devices, particularly an injection device in the form of a pen. The present disclosure is however not limited to such application and may equally well be deployed with other types of drug delivery devices, particularly with another shape than a pen.

Figure 1:
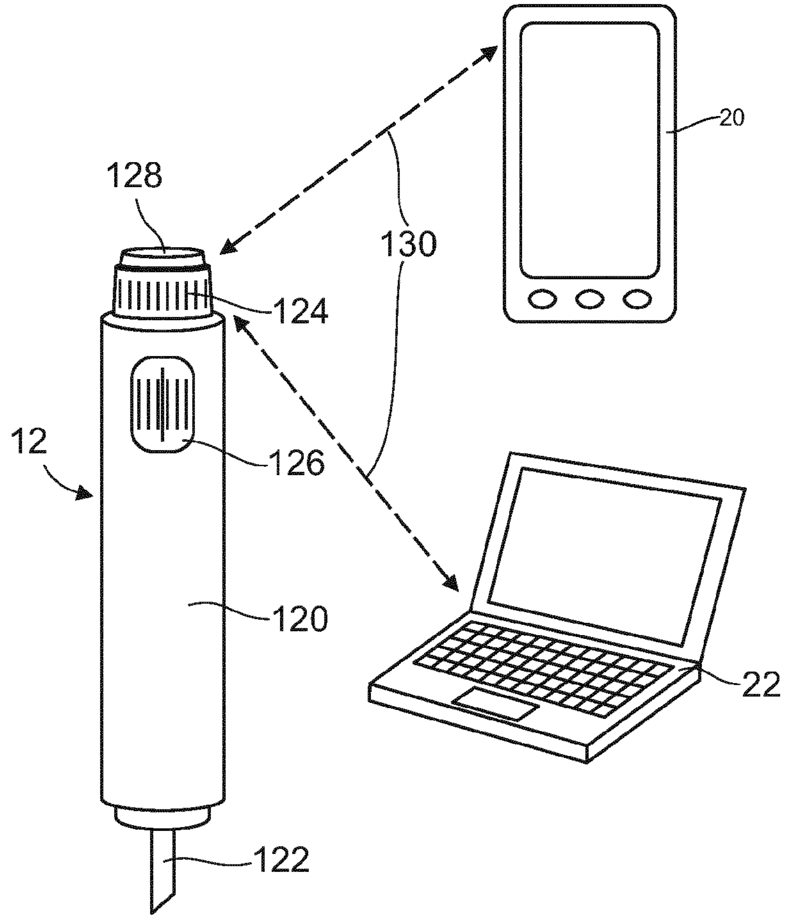
FIG. 1 shows an embodiment of a drug delivery device comprising a wireless data communication circuitry.

FIG. 1 shows a drug delivery device 12 in the shape of an insulin injection pen. The device 12 comprises an elongated body 120 having a pen-like shaped form for holding a drug cartridge and a dosage selection and delivery mechanism. At the lower end of the body 120, a syringe 122 for expelling a drug dosage and injecting this dosage in a patient's body is provided. The body 120 comprises at its other, upper end a dial knob 124 for selecting a drug dosage and an injection knob 128 for delivery of a selected dosage. In an alternative device the dial knob may also be the injection knob. A user of the device 12 selects a dosage by rotating the dial knob 124 around the longitudinal axis of the body 120. The selected dosage is shown on a display 126 integrated in the body 120. After dosage selection, the user may press the injection knob 128 in the direction of the longitudinal axis for expelling the selected dosage via the syringe 122 into a patient's body. The dosage selection and delivery mechanism contained in the body may comprises electronics (not visible in FIG. 1) for detecting and for storing and transmitting selected and delivered dosages.

A wireless data communication circuitry may be integrated in the device 12 or attached to the device 12 for example as an accessory, which can be clipped on the dial knob 124. The wireless data communication circuitry may be part of an electronics comprising wireless communication means for establishing a communication link 130 with an external device such as a smartphone 20 or a laptop computer 22, which may be paired with the wireless communication means. The term "paired" may mean that the wireless data communication circuitry and the external devices 20, 22 share some secret data such as cryptographic keys for establishing and/or securing data exchange.

The wireless data communication circuitry may be configured for establishing a long-range wireless communication via radio frequency communication such as a Bluetooth® communication link 130 with the external devices 20, 22 over a distance of at least several centimeters, particularly at least one meter, and more particularly several meters. The maximum distance provided for communication may depend on the power supply requirements of the accessory 10. For example, when the accessory 10 is powered by a one-time usable battery, which can last several months, at least a year or even longer, the maximum distance may be configured by reducing the power requirements of the wireless data communication circuitry to meet the desired battery lifetime. The communication link 130 may be secured due to a pairing process initially made for enabling the communication.

Figure 2:
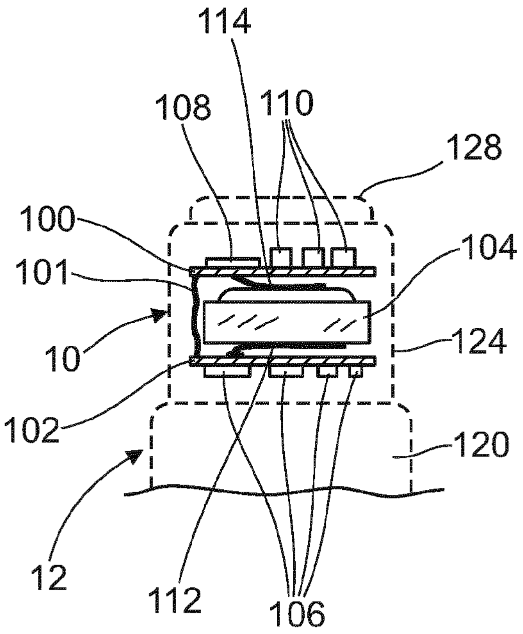
FIG. 2 shows an embodiment of an electronics for a drug delivery device as shown in FIG. 1 and comprising a printed circuit board with a wireless data communication circuitry.

FIG. 2 shows the electronics 10 comprising the wireless data communication circuitry and its integration the dial knob 124 of the drug delivery device 12. The electronics 10 comprises two printed circuit boards 100, 102 and a button cell battery 104. The battery 104 is "sandwiched" between a positive terminal 112 and a negative terminal 114 of a battery connector formed by printed circuit boards 100 and 102.

The printed circuit boards 100, 102 can be inflexible or flexible boards. The boards 100, 102 are shaped such that can be arranged within the dial knob 128. The boards 100 and 102 can be electrically connected via a flexible conductor comprising several electrical lines to exchange data and supply the boards 100 and 102 with electric current from the battery 104.

The battery 104 may be a lithium button cell battery of the type CR1225 having terminal voltage of about 3 volts and a capacity of several milliampere-hour, particularly about 38 milliampere-hour. The battery 104 may be selected to last for at least several months, and particularly of one or more years under a normal usage scenario of the drug delivery device 12.

Each board 100, 102 comprises electronic devices 106, 108, 110, which may be active and passive electronic devices such as integrated circuits, systems on chip (SoC), capacitors, resistors, etc. The electronic devices 106, 108, 110 may implement a measurement of a dosage selected and delivered by the drug delivery device 12 and may further implement a storage of the measured dosages and the wireless data communication circuitry for the wireless data exchange with the external devices 20 and 22.

The wireless data communication circuitry may comprise a wireless communication processor 108 and an arrangement of several capacitors 110 on the board 100. The wireless communication processor 108 may comprise a Bluetooth® communications circuitry 108 such as a Bluetooth® SoC CYBL10X6X from Cypress Semiconductor Corporation, San Jose, CA, US, a CC2640R2F wireless microcontroller for Bluetooth® low-energy applications from Texas Instruments Incorporated, Dallas, TX, US, or an nRF52832 SoC from Nordic Semiconductor ASA, Trondheim, Norway.

Each capacitor of the arrangement of several capacitors 110 may be connected, particularly permanently in parallel to the positive terminal 112 and the negative terminal 114 of the battery connector. The capacitors 110 may be of the same type, for example only ceramic, film, polymer, mica, tantalum or electrolytic capacitors, or of different types, for example both ceramic and electrolytic capacitors.

Experiments have shown that an arrangement of "backup" capacitors, which are particularly permanently connected in parallel to the positive terminal 112 and the negative terminal 114 of the battery connector, may improve battery life. For example, for a button cell battery of the type CR1225, an arrangement of two or three ceramic capacitors with each having a capacity of 47 microfarads (μF) and two further capacitors each having a capacity of 220 μF, for example electrolytic capacitors or larger ceramic capacitors, turned out to be advantageous for increasing the battery lifetime of the battery.

Figure 3:
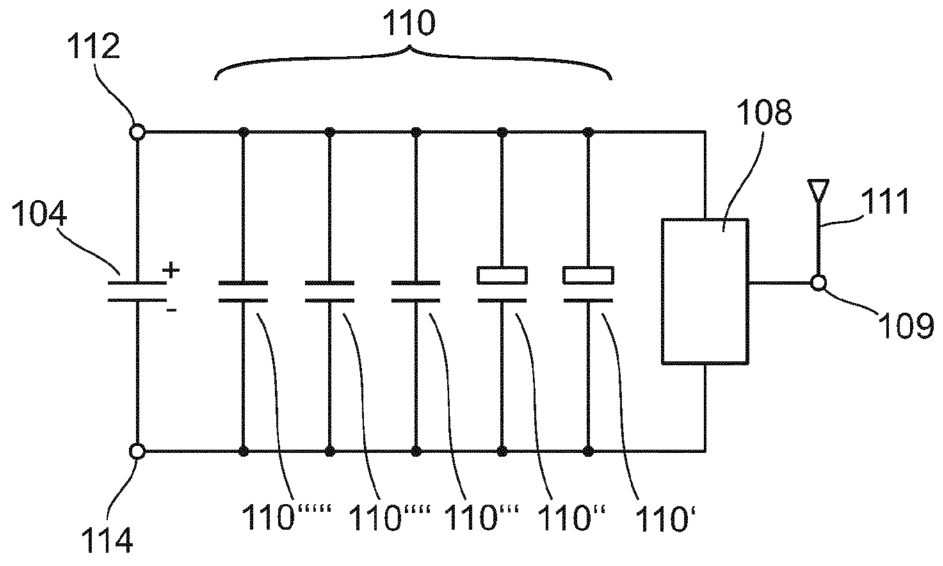
FIG. 3 shows schematics of an embodiment of a wireless data communication circuitry for a drug delivery device.

FIG. 3 shows schematics of a wireless data communication circuitry comprising a Bluetooth® SoC 108 as wireless communication processor and an arrangement of five "backup" capacitors 110 connected in parallel to the positive and negative terminals 112, 114 of the connector for the battery 104. The capacitors 110 may comprise two electrolytic capacitors 110' and 110'', which may comprise for example the same capacity of particularly 220 μF, and three ceramic capacitors 110''', 110'''', 110''''', which may comprise for example the same capacity of particularly 47 μF. All capacitors 110 are particularly permanently connected in parallel to the positive terminal 112 and the negative terminal 114 and the power supply pins of the SoC 108 such that a suddenly higher demand for electric current from the battery 104 by the SoC108, for example incurred by a data exchange operation via a Bluetooth® antenna 111 connected to an antenna connector 109, may be at least partly backed up with electric energy stored in the capacitors 110.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A drug delivery device comprising:
- a body;
- a dosage selection mechanism for selecting a drug dosage to be delivered;
- a delivery mechanism for delivering a selected drug dosage;
- at least one antenna for wireless communication;
- an actuator and a dose dial sleeve, wherein the electronics are arranged within the actuator, the actuator comprising at least one rotation sensor responsive to relative rotation of a sensed element fixed to the dose dial sleeve and the actuator during dose delivery; and
- electronics arranged within the body, wherein the electronics comprise a printed circuit board with a wireless data communication circuitry arranged on the printed circuit board;

wherein the wireless data communication circuitry of the electronics is coupled to the at least one antenna and comprises:
- a wireless communication processor for handling wireless data communication;
- a battery connector having a positive terminal and a negative terminal, the positive terminal and the negative terminal being connected to respective terminals of the wireless communication processor for supplying the wireless communication processor with electrical energy from a battery connectable to the battery connector; and
- an arrangement of at least two capacitors, each one of the capacitors being connected in parallel to the positive terminal and the negative terminal of the battery connector and provided for backing up the supplying of the wireless communication processor with electrical energy from the battery connectable to the battery connector.

2. The drug delivery device of claim 1, wherein the wireless data communication circuitry is configured to transmit data related to a dose of a drug delivered by the drug delivery device.

3. The drug delivery device of claim 1 comprising a cartridge of medication.

4. The drug delivery device of claim 1, wherein the electronics comprise a battery connected to the battery connector.

5. The drug delivery device of claim 1, wherein each one of the capacitors is permanently connected in parallel to the positive terminal and the negative terminal of the battery connector.

6. The drug delivery device of claim 1, wherein the wireless communication processor comprises a Bluetooth® communication circuitry with an antenna configured for Bluetooth® communication, wherein the Bluetooth® communication circuitry comprises a Bluetooth® Low Energy radio circuitry for wireless data communication.

7. The drug delivery device of claim 1, wherein the arrangement of at least two capacitors comprises four capacitors or five capacitors.

8. The drug delivery device of claim 7, wherein the arrangement of the four capacitors or the five capacitors comprises two capacitors with a capacity of 220 microfarads and two or three capacitors with a capacity of 47 microfarads.

9. The drug delivery device of claim 1, wherein the arrangement of the at least two capacitors comprises one or more of a ceramic capacitor; a film capacitor; a polymer capacitor; a mica capacitor; an electrolytic capacitor; and a tantalum capacitor.

10. The drug delivery device of claim 1, wherein the printed circuit board is configured to be arranged in or attached to the drug delivery device.

11. The drug delivery device of claim 10, wherein the printed circuit board is arranged in a drug injection pen or in an accessory attachable to the drug delivery device.

12. An accessory for attachment to a drug delivery device comprising:
- a housing configured for the attachment to the drug delivery device;
- at least one antenna for wireless communication being arranged within the housing;
- at least one rotation sensor responsive to rotation of a sensed element of the drug delivery device relative to the housing of the accessory during dose delivery; and
- electronics arranged within the housing, wherein the electronics comprise a printed circuit board with a wireless data communication circuitry arranged on the printed circuit board;
- wherein the wireless data communication circuitry of the electronics is coupled to the at least one antenna and comprises:
  - a wireless communication processor for handling wireless data communication;
  - a battery connector having a positive terminal and a negative terminal, the positive terminal and the negative terminal being connected to respective terminals of the wireless communication processor for supplying the wireless communication processor with electrical energy from a battery connectable to the battery connector; and
  - an arrangement of at least two capacitors, each one of the capacitors being connected in parallel to the positive terminal and the negative terminal of the battery connector and provided for backing up the supplying of the wireless communication processor with electrical energy from the battery connectable to the battery connector.

13. The accessory of claim 12, wherein the electronics comprise a battery connected to the battery connector.

* * * * *